US008701659B2

(12) United States Patent  (10) Patent No.: US 8,701,659 B2
Cosic  (45) Date of Patent: Apr. 22, 2014

(54) PATIENT VENTILATION SYSTEM WITH A GAS IDENTIFICATION UNIT

(75) Inventor: Nebojsa Cosic, Kista (SE)

(73) Assignee: Maquet Critical Care AB, Solna (SE)

( * ) Notice: Subject to any disclaimer, the term of this patent is extended or adjusted under 35 U.S.C. 154(b) by 805 days.

(21) Appl. No.: 12/666,798

(22) PCT Filed: Jun. 24, 2008

(86) PCT No.: PCT/SE2008/050760
§ 371 (c)(1),
(2), (4) Date: Nov. 15, 2010

(87) PCT Pub. No.: WO2009/002262
PCT Pub. Date: Dec. 31, 2008

(65) Prior Publication Data
US 2011/0041847 A1  Feb. 24, 2011

(30) Foreign Application Priority Data
Jun. 28, 2007  (WO) ................. PCT/EP2007/056483

(51) Int. Cl.
*A61M 16/00* (2006.01)
*A61M 15/00* (2006.01)
*A62B 7/00* (2006.01)

(52) U.S. Cl.
USPC ............................. 128/203.14; 128/204.18

(58) Field of Classification Search
CPC . A61M 16/18; A61M 16/01; A61M 16/0051; A61M 16/186
USPC ............ 128/202.22, 203.12, 203.14, 204.18, 128/204.21–204.23, 205.23, 205.24;73/1.34, 1.35, 23.2, 23.21; 702/24; 700/100, 285
See application file for complete search history.

(56) References Cited

U.S. PATENT DOCUMENTS

| 5,231,591 | A | 7/1993 | Flewelling et al. | |
| 5,619,986 | A * | 4/1997 | Werner et al. | 128/204.21 |
| 5,730,119 | A | 3/1998 | Lekholm | |
| 6,581,599 | B1 * | 6/2003 | Stenzler | 128/204.23 |
| 2003/0106554 | A1 | 6/2003 | de Silva et al. | |
| 2004/0149285 | A1 | 8/2004 | Wallen | |
| 2004/0211244 | A1 | 10/2004 | Cardelius et al. | |
| 2008/0078389 | A1 | 4/2008 | Xiao et al. | |

FOREIGN PATENT DOCUMENTS

| DE | 296 13 243 U1 | 11/1996 |
| WO | WO 88/04409 | 6/1988 |
| WO | WO 00/50890 | 8/2000 |

* cited by examiner

*Primary Examiner* — Melanie Hand
*Assistant Examiner* — Ned T Heffner
(74) *Attorney, Agent, or Firm* — Schiff Hardin LLP

(57) ABSTRACT

A patient ventilation system has a flow regulating and gas mixing assembly for providing oxygen to a first gas inlet and at least a second gas to a second gas inlet. The first and second gas inlets are connected to an inspiratory channel for conveying a delivered gas mixture including the oxygen and the at least second gas to a proximal tubing. The proximal tubing in turn is connected to an expiratory channel and connectable to a patient. The patient ventilation system further has a gas identification unit with which the at least second gas can be identified. The gas identification unit is arranged to measure actively a first value which is dependent on the characteristics of the at least second gas and attempt to identify the at least second gas based on said first value. The flow regulating and gas mixing assembly changes, at least temporarily, the concentration of the at least second gas in the delivered gas mixture if the gas identification attempt fails. The gas identification unit is further arranged to, subsequent to such a change in concentration, actively measure a second value which is dependent on the characteristics, and identify the at least second gas based on the second value alone or in combination with the first value.

17 Claims, 7 Drawing Sheets

PATIENT VENTILATION SYSTEM WITH A GAS IDENTIFICATION UNIT

BACKGROUND OF THE INVENTION

1. Field of the Invention

The present invention relates to a patient ventilation system as well as to a gas identification method for use in such a patient ventilation system.

2. Description of the Prior Art

Patient ventilation systems are employed in the administration of breathing gas to a patient, particularly in a hospital environment, and operate to control either or both the amount and the composition of the administrated breathing gas. As such, in the present context, the term "ventilation system" shall encompass ventilators, respirators and anesthesia machines as well as on-demand type face masks employed in medical environments. An example of such a patient ventilation system is described in EP 1 455 876 B1.

Patients in need of frequent respiratory treatment often show a severe increase in airway resistance. To overcome that resistance, a certain gas pressure is needed for moving gas into and out of the lungs of the patient. The pressure in the airway is directly related to the dynamic pressure gradient during the respiratory cycle, the flow rate of the gas, the density and viscosity of the gas, and the caliber and length of the airway.

It is well known to mix air with oxygen to increase the overall oxygen concentration delivered to the patient. To decrease the pressure required for moving gas through the airways, air can be substituted by "heliox", a mixture of helium and oxygen. As an inert gas, helium does not participate in any biochemical process of the body. However, as helium is the second lightest gas, it decreases the density and by that the required driving pressure. Typically, helium is mixed with at least 21% oxygen but depending on the specific conditions of the patient, this mixture can be altered.

Prior art ventilation systems normally have at least two gas inlets, one of which is connected to an oxygen source and the other to a second gas source such as an air source, a heliox source, a zenon source or a nitrous oxide source. If heliox is used, the distribution between helium and oxygen in the heliox mixture is typically 80% helium and 20% oxygen (heliox 80/20), or 70% helium and 30% oxygen (heliox 70/30). These external gas sources may be provided locally by pressurized bottles. Typically, there are often more gas supplies available for connection to the gas inlets than are required and care must be taken to ensure that the correct supplies are connected, especially as conventional gas sources are supplied with standardized pneumatic connection terminals. The prior art mentioned above discloses a gas identifier, which comprises a voltage divider adapted to provide an electrical interface to the ventilation system and a lookup table. The voltage divider includes a resistor having a resistance value unique for each gas supply. For a specific gas supply, a corresponding voltage drop will result as measured across the resistor. The lookup table comprises a list of voltage drops for the various gases, so that the gas mapping with the voltage drop is obtained from the lookup table.

With such an identification system, there may be an uncertainty if the correct voltage divider has been introduced or not. Therefore, the safety of such a system is deficient and barely provides more certainty than manually identifying the gas supply by simply looking at it and making the correct input to the ventilation system via the interface. In both cases and having in mind the stress situation in an ICU, there is no absolute knowledge about the gas, which actually is delivered to the ventilation system and there is no check up or safety control.

As is also known, e.g. from the prior art mentioned above, flow meters provide output signals which are dependent on the type of gas, i.e. if a flow meter is calibrated for measuring air, the meters output signal would deviate from the actual flow for another gas type like heliox 80/20. This is true even for other gases like nitrous oxide, zenon or other gas mixtures. The prior art therefore suggests means for correcting the calibration of any flow meter based on gas supply, which is identified in the above described way.

To ensure that a correct amount of oxygen is delivered to the patient, it is known to use an oxygen sensor, e.g. an oxygen cell, to measure the oxygen concentration in a gas mixture that is to be delivered to the patient. However, such an oxygen sensor cannot be used to identify what other gases or gas compositions, like air or heliox, are present in the gas mixture.

To increase the safety of any gas supply to a patient ventilation system, EP 1 441 222 A2 discloses monitoring means using an acoustic transceiver detecting the amplitude of the emitted acoustic energy propagated through a measurement chamber and generating a control signal from a comparison of the detected signal with a reference signal for the target gas, and generating a control signal to inhibit the gas flow through the system if the wrong gas is supplied.

It is also known in the art to measure the time of flight (TOF) for a sound pulse through a gas mixture, or the thermal conductivity of a gas mixture, in order to establish what other gases besides oxygen are present in that particular gas mixture.

However, since different gas compositions may have the same characteristics as regard the measured property (e.g. the ability of absorbing acoustic energy, conducting sound, conducting heat, etc.), the gas constituents of a gas mixture cannot always be unambiguously determined.

SUMMARY OF THE INVENTION

It is an object of the present invention to improve the reliability of the identification of any gas or gas mixture connected to a ventilation system via a gas inlet.

This and other objects are achieved according to the present invention by a patient ventilation system having flow regulating and gas mixing assembly that provides oxygen to a first gas inlet and at least a second gas to a second gas inlet. The first and second gas inlets are connected to an inspiratory channel for conveying a delivered gas mixture comprising the oxygen and the at least second gas to a proximal tubing, which proximal tubing in turn is connected to an expiratory channel and connectable to a patient. The patient ventilation system further has a gas identification unit with which said at least second gas can be identified. The gas identification means is arranged to measure actively a first value which is dependent on the characteristics of the at least second gas and attempt to identify said at least second gas based on said first value. The flow regulating and gas mixing assembly changes, at leas temporarily, the concentration of the at least second gas in the delivered gas mixture if the gas identification attempt fails. The gas identification unit is further arranged to, subsequent to such a change in concentration, actively measure a second value that is dependent on the characteristics, and to identify the at least second gas based on the second value alone or in combination with the first value.

If the gas identification unit is unable to identify the at least second gas that is mixed with oxygen, it is typically due to the fact that the measured value corresponds to more than one possible gas mixture composition. For example, the speed of sound through a gas mixture composed of a large volume fraction of oxygen and a small volume fraction of helium may be the same as in a gas mixture composed of 50 percent by volume air and 50 percent by volume oxygen. If the gas identification unit measures, e.g., the time of flight (TOF) for a sound pulse through the delivered gas mixture, the measured value would hence be the same for both gas mixtures, making them inseparable. Thus, it would be impossible to say whether the at least second gas is a heliox mixture or air. By temporarily changing the composition of the delivered gas mixture, e.g. by increasing the flow of the at least second gas for a short period of time, a new TOF value that is different from the first one can be obtained. The new measurement value can be used, alone or in combination with the value obtained before the change in delivered gas composition, to unambiguously identify the at least second gas.

According to an aspect of the invention, the flow regulating and gas mixing assembly changes the concentration of said at least second gas in the delivered gas mixture to an extent that makes the measured value fall outside a range of measurement values corresponding to more than one particular type of gas or gas mixture. This range of measured values corresponding to more than one particular type of gas or gas mixture will hereinafter be referred to as the ambiguity range as the gas identification means cannot unambiguously identify the at least second gas if the measured value falls within that range.

According to another aspect of the invention, the flow regulating and gas mixing assembly just slightly changes the concentration of said at least second gas in the delivered gas mixture, while the gas identification means is arranged to analyze the change in the measured value caused by the small change in concentration. In the exemplary case described above, in which the measured value is the TOF of a sound pulse through the delivered gas mixture, the change in TOF caused by a small change in oxygen concentration in the delivered gas mixture can be determined and used by the gas identification means to establish the identity of the second gas. If the second gas is a heliox mixture, a change in oxygen/helium volume fraction ratio will change the measured TOF most significantly. If the second gas is air, a small change in oxygen/air volume fraction ratio will have a very small impact on the measured TOF value. That is, by at least temporarily changing the concentration of the at least second gas in the delivered gas mixture and by studying, e.g., $\Delta TOF/\Delta O_2\%$ in the delivered gas mixture, the gas identification means can identify the second gas even when the measured TOF values fall within the ambiguity range.

Since the flow rate measured by conventional flow meters also depends on/the gas characteristics, the present invention may provide means for automatically correcting the calibration of any flow regulating and gas mixing units and/or flow meters in the ventilation system depending on the online measurement of the type of gas or gas mixture connected to the gas inlet. Since the gas supply is actively measured and identified, the system is not limited to gas bottles with a predefined gas mixture, for example Heliox 70/30 or 80/20, as provided from the suppliers, but will function properly with an arbitrary gas mixture. Thus the system will function very well even in rebreathing setups where expensive gases like Zenon are used, and where the expired gas is directly reused after CO2 has been removed by a filter. In such a situation, the supplied gas will differ in its mixture over time, but the system will always identify the mixture and correct the flow regulation and gas mixing units and/or flow meters accordingly. In addition, the ventilation system will detect if an erroneous gas bottle is unintentionally connected to the ventilation system. Thereby the ventilation system according to the present invention is less vulnerable to human errors than most prior art ventilation systems.

The gas identification means can be arranged anywhere in the gas flow path after the mixing point at which the oxygen and the at least second gas are mixed, i.e. after the point at which the first and the at least second inlets of the ventilation system are connected to a common inspiratory channel for conveying the delivered gas mixture to a patient. Although the gas identification unit can be disposed in the proximal tubing that is connectable to a patient, or even in the expiratory channel conveying expiration gases away from the patient, it is preferably arranged in the inspiratory channel, close to the mixing point at which the oxygen and the at least second gas are mixed. By arranging the gas identification unit close to the mixing point, system delays are reduced, allowing a change in the delivered gas composition to have a quicker impact on the measured value and hence allowing quicker identification of the at least second gas. Depending on the actual placement of the identification unit, other factors like CO2 or humidity may have to be taken into account. None the less, identification is possible at all places downstream the mixing point.

According to an aspect of the invention, the output signal from the identification unit is displayed on an interface connectable to the ventilation system, to show the user of the system which gas has been identified.

According to another aspect of the invention, the output signal of the identification unit will generate an alarm if the connected gas is not identified or if the identifies gas or gas mixture is not allowed, e.g. if 100% helium is identified.

According to yet another aspect of the invention, flow meters already existing in the ventilation system are simultaneously used as identification means, preferably flow meters using transit time technology. Thereby, the number of components in the system can be minimized.

There are a number of characteristics which differ for different types of gases or gas mixtures, e.g. the speed of sound through the gas or the thermal conductivity. The speed of sound can be measured with an ultrasonic transducer and the thermal conductivity can be measured with a heated thermistor or thermal resistor. However, the invention is not limited to the use of these particular gas characteristics for identifying the at least second gas. Any properties or characteristics that differ from gas to gas, or gas mixture to gas mixture, to an extent that is measurable with the gas identification means, may be used.

BRIEF DESCRIPTION OF THE DRAWINGS

A more complete appreciation of the invention disclosed herein will be obtained as the same becomes better understood by reference to the following detailed description when considered in conjunction with the accompanying figures briefly described below.

DESCRIPTION OF THE PREFERRED EMBODIMENTS

Figure 1:
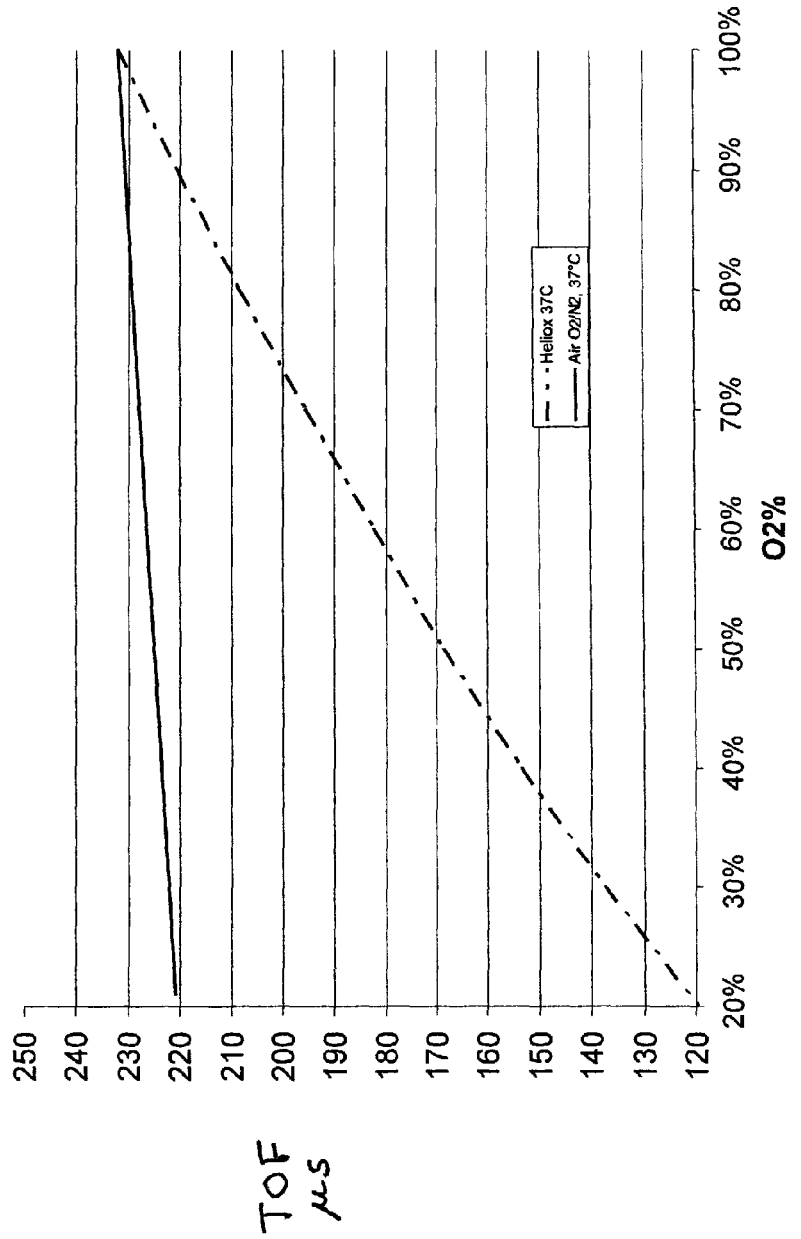
FIG. 1 shows a principle of gas identification using transit time technology.

FIG. 1 shows the principle of the gas identification using e.g. an ultrasound transceiver which measures the time of flight (TOF) for a sound pulse passing through the gas to be identified or, if it is done in the expiration line of the system, the expired gas including the gas to be identified. In this latter case, humidity and CO2 concentration can be estimated. FIG. 1 shows the TOF over the O2 concentration in percent for air as a solid line and for heliox as a dash-dotted line, starting on the left side of the diagram with 20% O2. Since helium concentration has a big influence on the speed of sound, there is a great difference in the time of flight between the sound pulses traversing heliox and the sound pulses traversing an equal distance in air. With a temperature of 37 degrees Celsius, a dry gas, and a specific measurement setup, the TOF for the sound pulse is approximately 122 µs in heliox 79/21 (21% O2), and approximately 222 µs in air. As can be seen from this diagram, increasing the O2 concentration changes the TOF for air only slightly, but for heliox substantially. Over the interval between 21% O2 and 100% O2 the TOF for heliox varies with 110 µs. As a result, the TOF measurements are equal to having a sensitive helium concentration meter and the composition of heliox, i.e. the mixture of helium and oxygen, can be identified with great accuracy. If the measured TOF stays within predefined limits, e.g. ±5 µs from the expected value for the gas mixture to be supplied, then the gas mixture has been identified. A greater deviation indicates that the wrong gas mixture has been connected to the gas inlet or that the identification does not work properly.

Figure 2:
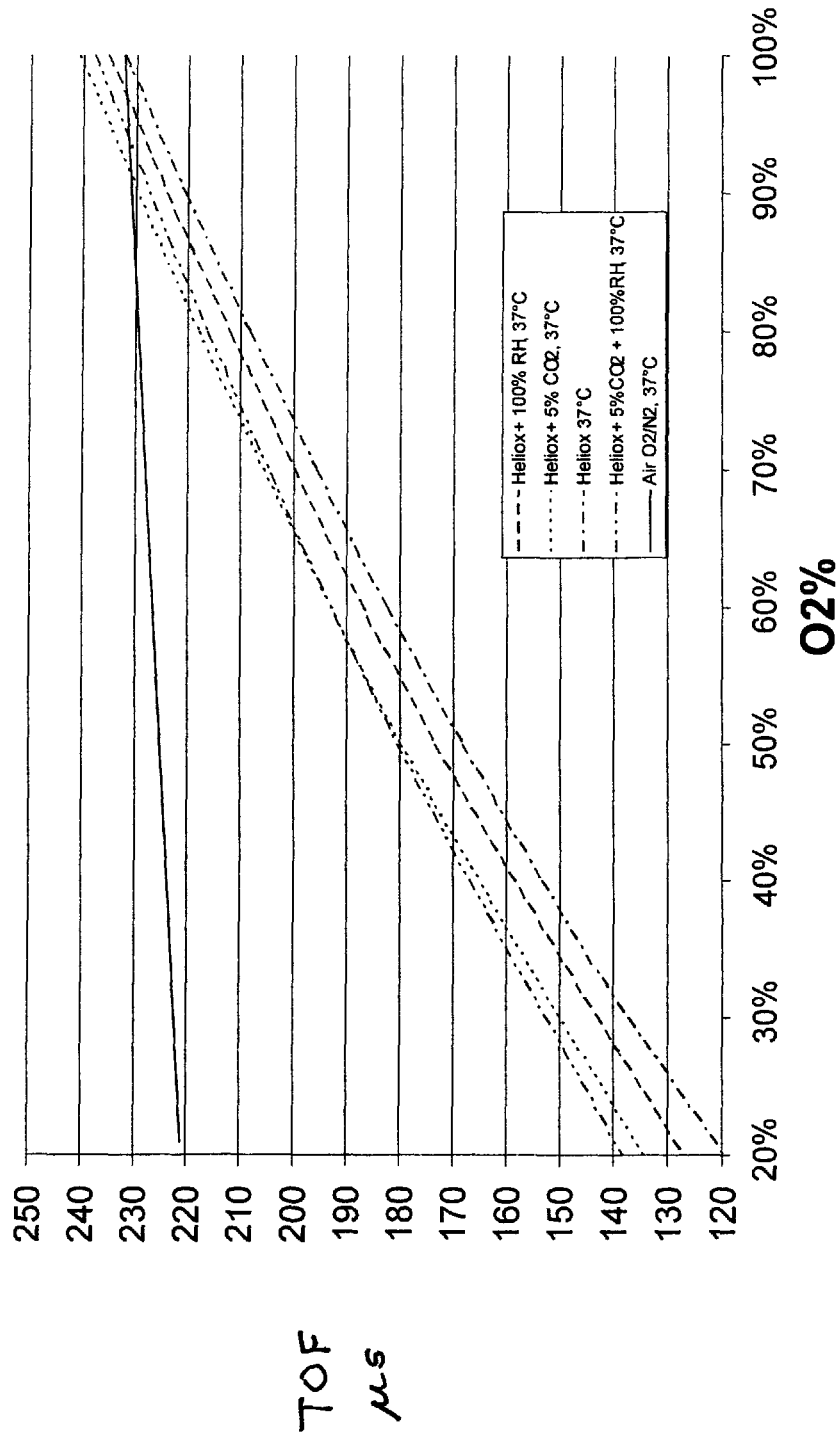
FIG. 2 shows the same principal for additional gas mixtures and conditions.

FIG. 2 shows the same diagram as FIG. 1 for compositions where heliox is mixed with 5% CO2 and/or has 100% relative humidity (RH). As can be seen from this diagram, if the CO2 concentration and/or humidity is known or can be estimated, the system still functions in a satisfactory way to identify the correct gas mixture.

Figure 3:
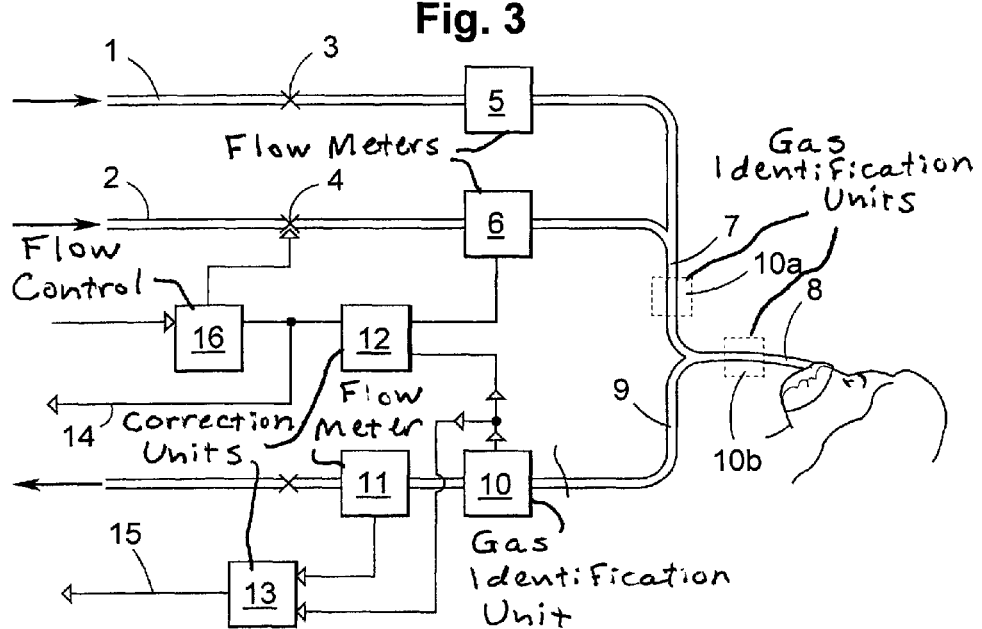
FIG. 3 shows an embodiment of a ventilation system comprising identification means for identifying gases connected to a gas inlet.

FIG. 3 shows an exemplary embodiment of a patient ventilation system having an identification unit 10 for identifying gases connected to a gas inlet. The system has two gas inlets 1 and 2, one for oxygen and one for air/heliox. From the inlets, the gases are let via inspiratory valves 3 and 4 and flow meters 5 and 6 to an inspiration channel 7, and further via a proximal tubing 8 to the airways of a patient. The expired gas passes through the expiration channel 9, the gas identification unit 10 and a flow meter 11. The gas identification unit 10 can be arranged anywhere in the gas flow path after (i.e. downstream) a mixing point $P_{mix}$ at which the oxygen and the air/heliox are mixed, i.e. after the point at which the first 1 and the second 2 inlets of the ventilation system are connected to a common inspiratory channel 7 for conveying a delivered gas mixture to a patient. For example, the gas identification unit 10 can be arranged in the inspiration channel 7 or the proximal tubing 8, without deviating from the general principal of the invention. Gas identification units 10a and 10b are depicted in these places in dashed lines.

In a ventilation system without gas identification means, the output signal from the flow meter 6 is fed to a flow control 16 as actual value. The flow control 16 compares this value with a set value and generates a control signal for the inspiration valve 4. The same closed loop flow control is provided for the O2 supply, but not depicted in the figure.

According to the present invention, the gas identification unit 10 measures actively a value which is dependent on the characteristics of the gas supplied via inlet 2 and tries to identify said gas based on the measured value. The gas identification means then generates a signal representative of the identified gas, e.g. air 21/79, heliox 80/20 or heliox 70/30. This signal can be fed to correction units 12 and 13 for correcting the flow value directly measured by the flow meters 6 or 11. Normally, the flow meters are calibrated for air and their output signal would deviate from the actual value for other gases like heliox. The correction units 12 or 13 compensate for such a deviation and make sure, that the flow control 16 receives a corrected actual value. In addition, the corrected flow signals are fed to an alarm and/or display (not shown), as indicated by arrows 14 and 15.

In this embodiment, the correction of the flow takes place in the correction units 12, 13. The correction units 12, 13 can also be part of the flow meters 6, 11 so that the output signal from the gas identification units 10 corrects the calibration of the flow meters 6, 11.

Figure 4:
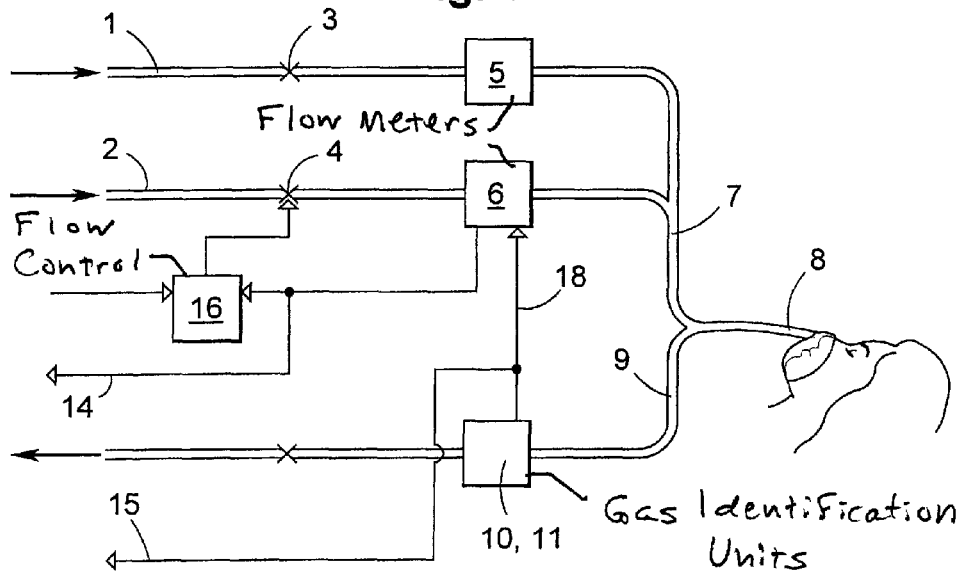
FIG. 4 shows another embodiment of such a system.

FIG. 4 shows another exemplary embodiment of the present invention, in which the same reference numerals as in FIG. 3 are used for similar components.

The only but important difference between the embodiments shown in FIG. 3 and FIG. 4 is of a specific flow meter 11, which uses transit time technology such as ultra sound propagation to measure the flow. This measurement technology can simultaneously be used to identify the gas passing through the flow meter 11, either by utilizing the speed of sound or the damping of a sound pulse traversing the gas flow, as is generally known in the art. As an advantage, no separate gas identification units is necessary. The output signal from this combined gas identification unit/flow meter 10, 11 is fed via line 18 to the flow meter 6 to correct its calibration. It is also possible to include a means for correction between the flow meter 6 and the flow control 16 as in FIG. 3. As mentioned before, other characteristics of the gas to be identified, e.g. the thermal conductivity thereof, could also be used in the identification process without deviating from the principle of the invention.

Figure 5:
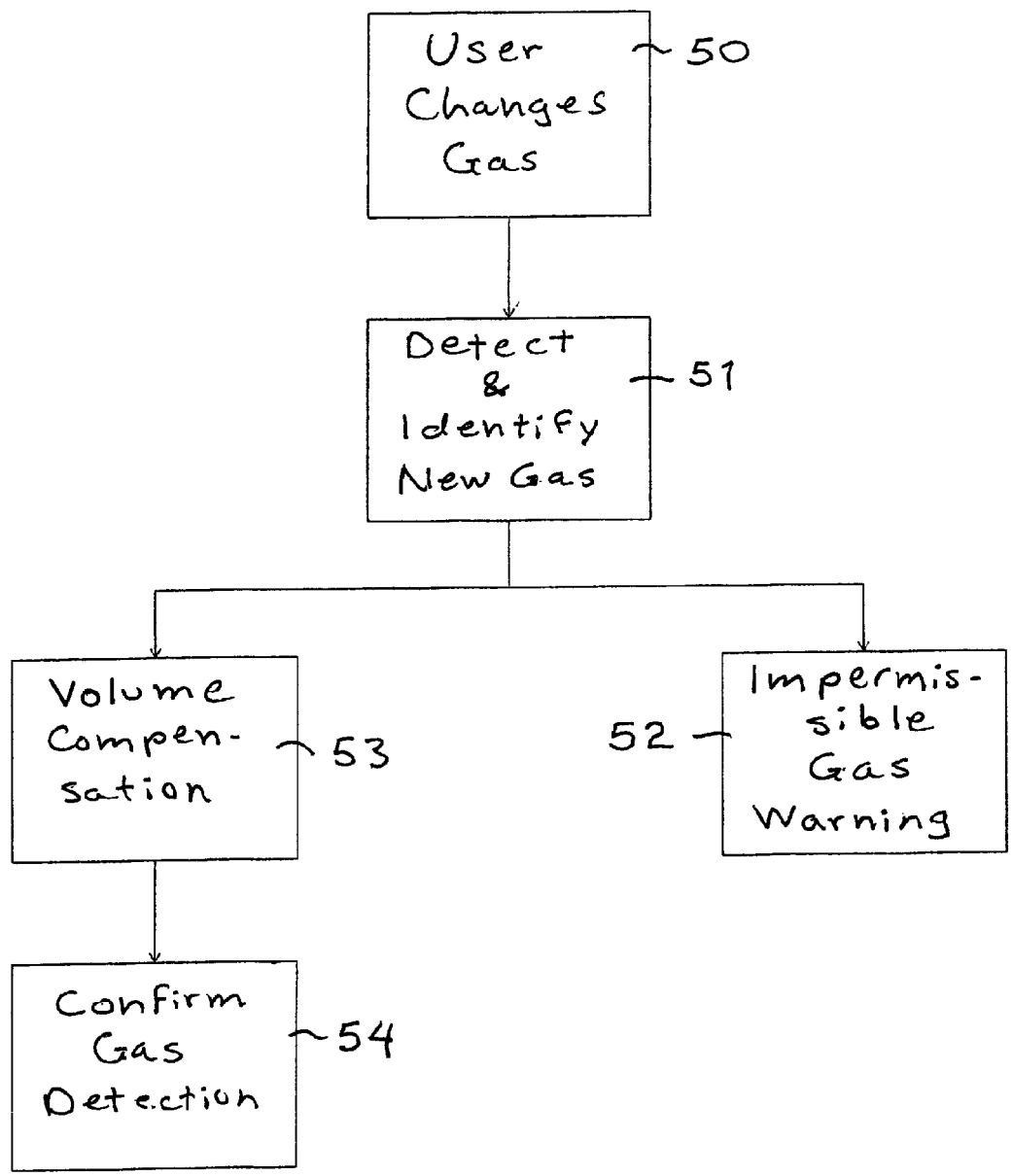
FIG. 5 shows a flow diagram for a gas exchange in a standby situation.
Figure 6:
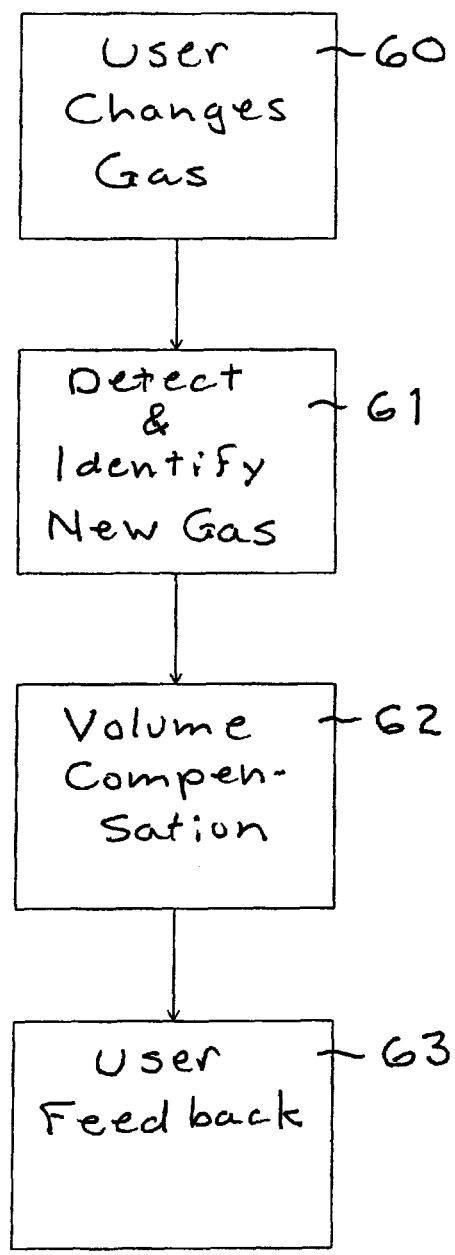
FIG. 6 shows a flow diagram for a gas exchange during ventilation.

In all embodiments, the possibility to generate an alarm if the identified gas deviates from the gas the user has chosen, or if no gas is identified, increases the overall safety of the ventilation system. The display on an interface facilitates the understanding of what is going on in the system. Another advantage of this automatic gas identification and flow correcting system according to the invention lies in the possibility to check the gas supply in a pre-use check when a new gas supply is connected to one gas inlet under standby, or even during ventilation. FIGS. 5 and 6 show possible flow diagrams for these two cases.

FIG. 5 illustrates a flow diagram for a gas exchange in a standby situation. In step 50, a user changes the gas in the ventilation system and, in step 51, the gas identification units 10, 10a, 10b detects and identifies the new gas. If the detected gas or gas mixture is not allowed, the procedure proceeds to step 52 in which the system warns the user by means of a suitable alarm signal, e.g. by displaying an alarm symbol on the interface or by generating a sound alarm. If, on the other hand, the detected gas or gas mixture is allowed, the procedure proceeds to step 53 in which the system compensates the set volume, i.e. the breathing gas volume provided to a patient during ventilation, in dependence of the properties of the new gas. Finally, in step 54, the system confirms the gas detection by, e.g., a notification displayed on the interface, and further prompts the user to review the ventilation settings in order to ensure a correspondence between the ventilator settings and the new gas.

FIG. 6 shows a flow diagram for a gas exchange during ventilation. The procedure is identical to the procedure illustrated in FIG. 5, in the case where an allowed gas or gas mixture is detected by the gas identification units 10, 10a, 10b. Consequently, in step 60, a user changes the gas used in the ventilation system whereupon the system detects the new gas in step 61. In step 62, the system compensates the set volume based on the detected gas and, in step 63, the system gives the user feedback on the gas detection and prompts the user to review the ventilator settings.

Figure 7:
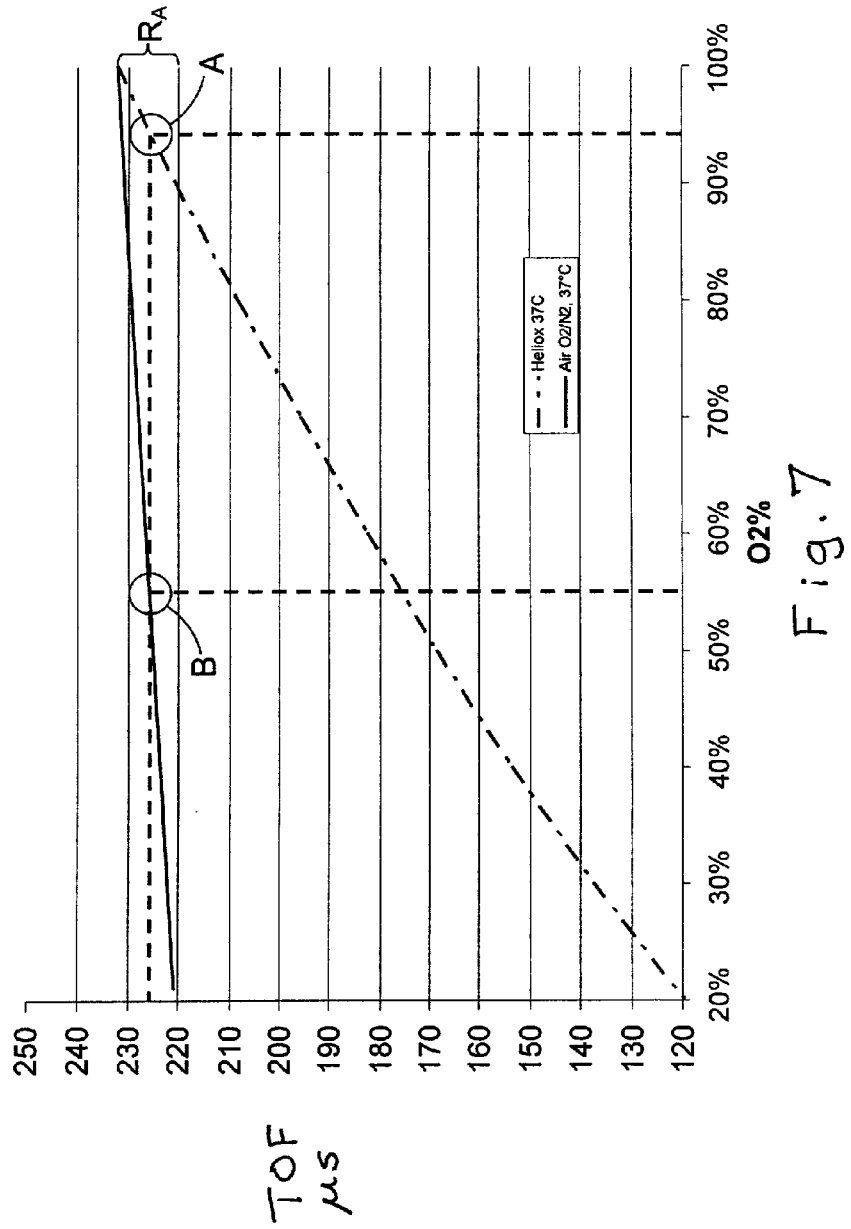
FIG. 7 illustrates a scenario in which the present invention enables identification of a gas mixture.

FIG. 7 illustrates a scenario in which the above described principle for gas identification suffers from drawbacks. The diagram in FIG. 7 corresponds to the diagram shown in FIG. 1 and hence shows the principle of gas identification using an ultrasound transceiver which measures the TOF for a sound pulse passing through a gas mixture whose gas constituents, at least partly, are to be determined. The solid line illustrates the TOF over the O2 concentration in percent for air, and the dash-dotted line illustrates the TOF over the O2 concentration in percent for heliox, starting on the left side of the diagram with 20% O2.

In this exemplary scenario, the second gas that is supplied via the second inlet 2 (see FIGS. 3 and 4) is assumed to be a heliox mixture having a relatively low percentage by volume of helium. After being mixed with pure oxygen at the mixing point $P_{mix}$, the oxygen content in the gas mixture that is to be delivered to the patient can be high. In this example, the gas identification unit of the ventilation system measures a TOF of 226 μs for a sound pulse traversing a given distance of the gas mixture. This TOF value is seen to correspond to a heliox/oxygen mixture having an oxygen volume fraction of 94%, as indicated by the measurement point denoted by 'A' along the dash-dotted line that represents heliox. However, the measured TOF value also corresponds to an air/oxygen mixture having an oxygen volume fraction of 55%, as indicated by a point denoted 'B' along the solid line that represents air. Thus, the gas identification means cannot unambiguously identify the gas supplied via inlet 2 as there is more than one possible gas mixture corresponding to the measured TOF value. As seen in the diagram, this problem arises for all TOF values within a value range denoted by '$R_A$', which range in this exemplary case includes TOF values between approximately 220 and 232 μs. Such a range in which the values do not allow for unambiguous identification of the second gas will hereinafter be referred to as an ambiguity range, $R_A$.

To overcome this problem, the flow regulating and gas mixing assembly of the ventilation system according to the invention is arranged to change, at least temporarily, the concentration of the second gas in the delivered gas mixture if the gas identification means fails to unambiguously identify said second gas based on the measured value.

By temporarily changing the composition of the delivered gas mixture, a new or second value of the measured gas characteristics (in this particular case the ability to conduct sound) which deviates from the value obtained before the change can be obtained. The new measurement value can be used, alone or in combination with the value obtained before the change, to unambiguously identify the second gas or gas mixture.

In a first embodiment of the invention, the flow regulating and gas mixing assembly changes the concentration of the second gas in the delivered gas mixture to such an extent that the measured value falls outside the ambiguity range, $R_A$. This is typically achieved by increasing the flow of the second gas such that the volume fraction of oxygen in the delivered gas mixture decreases. Of course, the same result may be achieved by decreasing the flow of oxygen, or increasing the flow of the second gas while decreasing the flow of oxygen so as to keep the delivered total volume constant. In the example illustrated in FIG. 7, in which the second gas is assumed to be a heliox mixture and the measured value is the TOF for a sound pulse travelling a given distance in the delivered gas mixture, such a decrease in volume fraction of oxygen would move measurement point A towards the left, along the dash-dotted heliox line, resulting in a measured TOF value falling below the ambiguity range, $R_A$. When the gas identification means measures a TOF below 220 μs, it can identify the second gas as heliox.

In a second embodiment of the invention, the flow regulating and gas mixing assembly alters the concentration of the second gas in the delivered gas mixture only slightly, and the gas identification means is arranged to analyze the change in measured value caused by the small change in concentration. This is also typically achieved by increasing the flow of the second gas such that the volume fraction of oxygen in the delivered gas mixture decreases. As seen in FIG. 7, a small decrease in percentage by volume of oxygen in the gas mixture will result in a significant decrease in TOF if the second gas is heliox, while, if the second gas is air, the same decrease in percentage by volume of oxygen would change the measured TOF value only slightly. By measuring the TOF before and after a small change in concentration of the second gas in the delivered gas mixture, and comparing the two measured values, the gas identification means can identify the gas. That is, the gas identification unit, according to this second embodiment of the invention, identifies the second gas by studying the derivative, or rate of change, of the measured value with respect to the oxygen concentration in the analyzed gas mixture. In this particular case the studied quantity is hence the derivative of TOF with respect to oxygen concentration, $\Delta TOF/\Delta O_2\%$.

The second embodiment described above is advantageous because a very small change in concentration of the second gas in the analyzed gas mixture is sufficient to identify the second gas. In contrast to the first embodiment, the change in concentration does not have to be big enough to make the measured TOF value fall outside the ambiguity range, $R_A$. That only a small change in concentration is sufficient is particularly true when the gas identification means is located close to the mixing point $P_{mix}$ (see FIGS. 3 and 4) in the ventilation system such that a small change in composition of the delivered gas mixture has an immediate impact on the measured value. Therefore, the gas identification means is preferably, but not necessarily, located in the position illustrated with reference numeral 10a in FIG. 3. As will be understood by a skilled person, a change in the delivered gas mixture composition would also change the volume fraction ratio between the gas constituents in the gases exhaled by a patient connected to the system. Therefore, the principle is applicable also when the gas identification means is disposed in the expiration branch 9 of the ventilation system.

It should be understood that the problem arising when the measured value corresponds to more than one possible gas mixture is not only associated with TOF measurements. The same problem may occur also when measuring other physical quantities of which values depend on the characteristics of the second gas, such as, for example, thermal conductivity. There may still exist a critical value range, corresponding to the ambiguity range denoted by '$R_A$' in FIG. 7, in which the values correspond to more than one possible gas mixture composition. It should thus be appreciated that the above described principle of at least temporarily changing the concentration of the second gas in the analyzed gas mixture in order to unambiguously identify the second gas is not limited to gas identification based on TOF measurements.

Once again with reference to FIG. 3, an exemplary implementation of the above discussed functionality will now be described. The gas identification units 10, 10a, 10b can be arranged to, when unable to identify the second gas based on the performed measurements, generate a signal indicating that this is the case and send the signal to the flow control means 16. Upon reception of said signal, the flow control units 16 regulates the inspiratory valve 4 such that the flow of the second gas through gas inlet 2 increases, thereby decreasing the volume fraction of oxygen in the gas mixture downstream the mixing point $P_{mix}$. This decrease in volume fraction of oxygen makes it possible for the gas identification units 10, 10a, 10b to unambiguously identify the second gas supplied via inlet 2 as described above. Various actions can then be taken based on the result of the gas identification. Such actions may involve, e.g., the displaying of the gas identity on a graphical user interface and the correction of flow values measured by flow meters 6, 11 in the ventilation system, or, if the identified gas deviates from a preset gas type, the quenching of the supply of the second gas and/or the generation of an alarm signal. As aforementioned, although not illustrated in FIG. 3, there is typically a flow control unit connected to the flow meter 5 and the inspiration valve 3 in the oxygen supply inlet 1, to form a closed loop oxygen flow control in accordance with the closed loop flow control 4, 6, 16 for the second gas supply in the second gas inlet 2. Typically, the ventilation system also has a central control unit (not shown) controlling the flow control units in each gas inlet 1, 2 to make them cooperate. It should be understood that the gas identification units 10, 10a, 10b can be arranged to communicate that gas identification was unsuccessful to either any or both of the flow control units in the respective gas inlets 1, 2, and/or to such a central control unit, whereupon the control unit(s) carries into effect the change in delivered gas composition.

An important ventilation parameter is the oxygen concentration delivered to the ventilated patient. It is desirable to keep this parameter constant over time. The proposed principle of at least temporarily changing the concentration of the second gas in the delivered gas mixture to render possible identification of said second gas yields a temporary change in volume fraction of oxygen delivered to the patient. Therefore, the ventilation system according to the invention is preferably arranged to compensate for such a temporary change in delivered oxygen content. No matter whether the concentration of the second gas in the delivered gas mixture is increased or decreased in the first place, the flow regulating and gas mixing assembly of the ventilation system can be arranged to, subsequent to the first change in concentration, compensate by for a short period of time changing the oxygen/second gas volume fraction ratio the other way around. Thereby, the average oxygen concentration delivered to the patient can be kept equal to a preset reference value.

Figure 8:
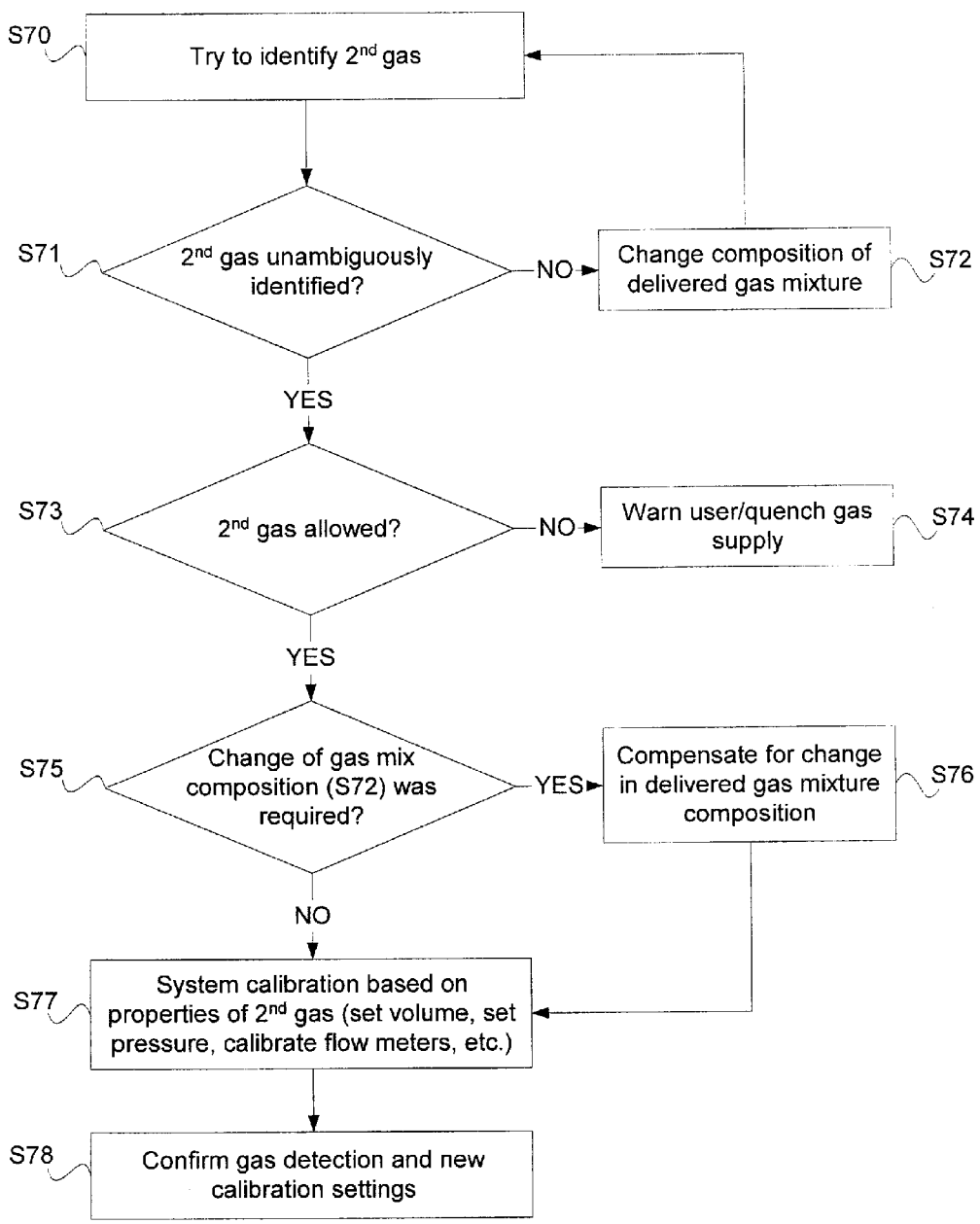
FIG. 8 shows a flow diagram illustrating a gas identification method according to the invention.

FIG. 8 illustrates a flow diagram illustrating a method for gas identification according to the invention. When describing the flow diagram, simultaneous reference will be made to the system components illustrated in FIGS. 3 and 4.

In step S70, the gas identification units 10, 10a, 10b try to identify the second gas supplied via gas inlet 2 by actively measuring a value which is dependent on the characteristics of said at least second gas. The measurement can take place in any of the inspiration channel 7, the proximal tubing 8 or the expiration channel 9 of the ventilation system. Gas identification can be initiated upon gas exchange in a standby situation or upon gas exchange during ongoing ventilation, but it can also be performed continuously or periodically during ongoing ventilation.

In step S71, it is determined whether the gas identification units 10, 10a, 10b, failed or succeeded to unambiguously identify the second gas in step S70. If the identification was unsuccessful due to the fact that the measured value indicated that the second gas could be any of two or more gas types, the method proceeds to step S72.

In step S72, the flow regulating and gas mixing assembly 3, 4, 5, 6, 16 of the ventilation system changes the concentration of the second gas in the delivered gas mixture, typically by slightly increasing the flow of the second gas, whereupon the method returns to step S70.

This time, in step S70, the gas identification means obtains a new or second measurement value of the analyzed gas characteristic, which new value is different from the first obtained value due to the change in gas composition performed in step S72. The gas identification means then unambiguously identifies the second gas. If the change in gas composition made in step S72 was sufficient to make the new value fall outside an ambiguity value range, such as the ambiguity range $R_A$ discussed above with reference to FIG. 7, the new value itself is sufficient for identifying the second gas. If, on the other hand, the change in concentration of the second gas made in step S72 is very small, the difference between the first value obtained before the change in gas composition and the second value obtained after the change in gas composition can be used to identify the second gas.

In step S71, it is established that the gas identification attempt in step S70 was successful, whereupon various optional actions may be taken.

In a first optional step, S73, it is determined whether the identified gas is allowed, i.e. whether the identified second gas corresponds to a preset gas or gas mixture. If not allowed, the method may proceed to a step S74 in which the system warns the user that an unallowable gas is connected to the ventilation system and/or automatically quenches the supply of the second gas.

In a second optional step, S75, it is determined whether a change in delivered gas mixture composition (i.e. step S72) was required in order to identify the second gas. If so, the method may proceed to a step S76 in which the change is compensated in order to keep the average oxygen concentration delivered to the patient equal to a preset reference value.

Typically, in an optional step S77, a system calibration is performed based on the properties of the detected gas. This system calibration may include, e.g., adjustments of the volume or pressure of the breathing gas delivered to the patient during ventilation, corrections of the flow values measured by flow meters 6, 10 in the ventilation system, etc. The system calibration may also, as the gas identification units 10, 10a, 10b is able to determine the composition of the delivered gas, involve the step of calibrating the flow regulating and gas mixing units 2, 4, 5, 6, 16 of the ventilation system in case the determined gas composition differs from a preset reference gas mixture composition. For example, if the system operator has programmed the ventilation system to deliver a gas mixture comprising 60 percentage by volume of oxygen to a patient but the value measured by the gas identification means indicates that the delivered gas mixture only contains 50 percentage by volume of oxygen, the calibration of the flow regulating and gas mixing assembly of the ventilation system can be corrected. Typically, this is achieved by increasing the flow of oxygen while simultaneously decreasing the flow of the second gas so as to keep the total gas volume delivered to the patient as close as possible to the preset reference value. When used for this purpose, the gas identification units 10, 10a, 10b forms a part of a closed loop flow control system ensuring that the composition of a gas mixture delivered to a patient always corresponds to a preset reference gas mixture composition. Preferably, the ventilation system is also arranged to generate an alarm signal if the determined composition of the delivered gas mixture differs substantially from the preset reference composition.

In a last optional step S78, the identity of the second gas, the determined composition of the delivered gas mixture, and/or any new calibration settings of the ventilation system are displayed to the system operator on a graphical user interface.

It should be evident from the foregoing that various modifications can be made to the embodiments of this invention without departing from the scope thereof, which would be apparent to those skilled in the art.

I claim as my invention:

1. A patient ventilation system comprising:
   a breathing circuit comprising an inspiration channel and an expiration channel adapted for connection to a patient;
   a flow regulating and gas mixing arrangement connected to said breathing circuit that delivers a gas mixture comprising oxygen and at least a second gas to the patient via the expiratory channel;
   a control unit configured to control operation of said flow regulating and gas mixing arrangement;
   a gas identification unit configured to initiate an attempt to identify said second gas by actively measuring a first value dependent on a characteristic of said second gas that distinguishes said second gas from gases other than said second gas;
   said control unit being configured to monitor said attempt by said gas identification unit to identify said second gas and, if said attempt fails to identify said second gas, in response to said attempt failing to identify said second gas, to cause said flow regulating and gas mixing arrangement to, at least temporarily, change a concentration of said second gas in said gas mixture; and
   said gas identification unit being configured, after said change in concentration, to initiate a subsequent attempt to identify said second gas by actively measuring a second value dependent on said characteristic of said second gas and to identify said second gas from said second value alone or in combination with said first value.

2. A patient ventilation system as claimed in claim 1 wherein said control unit is configured to cause said flow regulating and gas mixing arrangement to change said concentration of said second gas in said gas mixture by causing said second value to be outside of a value range that encompasses all values corresponding to more than one predetermined type of gas or gas mixture, and wherein said gas identification unit is configured to identify said second gas, in said subsequent attempt, dependent on said second gas value alone.

3. A patient ventilation system as claimed in claim 1 wherein said gas identification unit is configured to identify said second gas based on a difference between said first value and said second value caused by said change in concentration of said second gas in said gas mixture.

4. A patient ventilation system as claimed in claim 1 wherein said gas identification unit is located in said inspiration channel.

5. A patient ventilation system as claimed in claim 1 comprising proximal tubing adapted to connect said expiration channel to said patient, and wherein said gas identification unit is located in said proximal tubing or in said expiration channel.

6. A patient ventilation system as claimed in claim 1 wherein said control unit is configured to cause said flow regulating and gas mixing arrangement to at least temporarily change said concentration of said second gas in said gas mixture by at least temporarily increasing a flow of said second gas in said flow regulating and gas mixing arrangement.

7. A patient ventilation system as claimed in claim 1 wherein said control unit is configured to cause said flow regulating and gas mixing arrangement, after said change in said concentration of said second gas in said gas mixture, to compensate for said change by adjusting at least one of a flow of oxygen or a flow of said second gas to cause an average volume fraction of oxygen in said gas mixture over time to be substantially equally to a predetermined reference value.

8. A patient ventilation system as claimed in claim 1 wherein said gas identification unit is configured to measure, as said characteristic of said second gas that distinguishes said second gas from gases other than said second gas, a characteristic of said second gas selected from the group consisting of speed of sound in said second gas and thermal conductivity of said second gas.

9. A method for operating a patient ventilation system, comprising the steps of:
   connecting a breathing circuit comprising an inspiration channel and an expiration channel to a patient;
   through a flow regulating and gas mixing arrangement connected to said breathing circuit, delivering a gas mixture comprising oxygen and at least a second gas to the patient via the expiration channel;
   with a computerized control unit, controlling operation of said flow regulating and gas mixing arrangement;
   with a gas identification unit, initiating an attempt to identify said second gas by actively measuring a first value dependent on a characteristic of said second gas that distinguishes said second gas from gases other than said second gas;
   in said control unit, monitoring said attempt by said gas identification unit to identify said second gas and, if said attempt fails to identify said second gas, in response to said attempt failing to identify said second gas, automatically causing said flow regulating and gas mixing arrangement to, at least temporarily, change a concentration of said second gas in said gas mixture; and
   in said gas identification unit, after said change in concentration, initiating a subsequent attempt to identify said second gas by actively measuring a second value dependent on said characteristic of said second gas and identifying said second gas from said second value alone or in combination with said first value.

10. A method as claimed in claim 9 comprising, from said control unit, causing said flow regulating and gas mixing arrangement to change said concentration of said second gas in said gas mixture by causing said second value to be outside of a value range that encompasses all values corresponding to more than one predetermined type of gas or gas mixture and, in said gas identification unit, identifying said second gas, in said subsequent attempt, dependent on said second gas value alone.

11. A method as claimed in claim 9 comprising, in said gas identification unit, identifying said second gas based on a difference between said first value and said second value caused by said change in concentration of said second gas in said gas mixture.

12. A method as claimed in claim 9 comprising locating said gas identification unit in said inspiration channel.

13. A method as claimed in claim 9 comprising connecting said expiration channel to said patient via proximal tubing, and locating said gas identification unit in said proximal tubing or in said expiration channel.

14. A method as claimed in claim 9 comprising, from said control unit, causing said flow regulating and gas mixing arrangement to at least temporarily change said concentration of said second gas in said gas mixture by at least temporarily increasing a flow of said second gas in said flow regulating and gas mixing arrangement.

15. A method as claimed in claim 9 comprising, from said control unit, causing said flow regulating and gas mixing arrangement, after said change in said concentration of said second gas in said gas mixture, to compensate for said change by adjusting at least one of a flow of oxygen or a flow of said second gas to cause an average volume fraction of oxygen in said gas mixture over time to be substantially equally to a predetermined reference value.

16. A method as claimed in claim 9 wherein said patient ventilation system comprises at least one flow meter, and comprising the additional step of calibrating said at least one flow meter dependent on the identity of said gas.

17. A method as claimed in claim 9 comprising measuring, as said characteristic of said second gas that distinguishes said second gas from gases other than said second gas, a characteristic of said second gas selected from the group consisting of speed of sound in said second gas and thermal conductivity of said second gas.

* * * * *